(12) United States Patent
Guharay et al.

(10) Patent No.: US 10,175,196 B2
(45) Date of Patent: Jan. 8, 2019

(54) HYBRID ION MOBILITY SPECTROMETER

(71) Applicant: The MITRE Corporation, McLean, VA (US)

(72) Inventors: Samar Kumar Guharay, Fairfax Station, VA (US); Herbert H. Hill, Jr., Pullman, WA (US)

(73) Assignee: The MITRE Corporation, McLean, VA (US)

( * ) Notice: Subject to any disclaimer, the term of this patent is extended or adjusted under 35 U.S.C. 154(b) by 417 days.

(21) Appl. No.: 14/302,361

(22) Filed: Jun. 11, 2014

(65) Prior Publication Data

US 2016/0202211 A1    Jul. 14, 2016

(51) Int. Cl.
*G01N 27/62* (2006.01)

(52) U.S. Cl.
CPC .................. *G01N 27/622* (2013.01)

(58) Field of Classification Search
CPC ........ G01N 27/622; H01J 49/00; H01J 49/02; H01J 49/26; H01J 49/40; H01J 49/403; H01J 49/43; H01J 49/426
USPC ................ 250/281, 282, 283, 286, 287, 290
See application file for complete search history.

(56) References Cited

U.S. PATENT DOCUMENTS

| | | | | |
|---|---|---|---|---|
| 5,905,258 A * | 5/1999 | Clemmer | ............. | G01N 27/622 250/282 |
| 6,459,079 B1 * | 10/2002 | Machlinski | .......... | G01N 27/622 250/286 |
| 7,985,949 B2 | 7/2011 | Rodier | | |
| 2005/0109930 A1 * | 5/2005 | Hill, Jr. | ................ | H01J 49/0431 250/286 |
| 2005/0253061 A1 * | 11/2005 | Cameron | ............. | G01N 27/624 250/287 |
| 2006/0071159 A1 * | 4/2006 | Hashimoto | .......... | G01N 27/622 250/287 |
| 2007/0158543 A1 * | 7/2007 | Clowers | ............... | G01N 27/622 250/282 |
| 2010/0129785 A1 | 5/2010 | Pris et al. | | |
| 2012/0228491 A1 * | 9/2012 | Wu | ...................... | G01N 27/622 250/282 |

FOREIGN PATENT DOCUMENTS

WO    WO 2013/098645 A2    7/2013

OTHER PUBLICATIONS

Ho, C. and Webb, S., *Gas Transport in Porous Media, Theory and Applications of Transport in Porous Media*, vol. 20, Springer, pp. 1-444 (2006).

Lamabadusuriya, M.R. et al., "Ionization, Transport, Separation, and Detection of Ions in Non-Electrolyte Containing Liquids," *Analytical Chemistry*, vol. 85, ACS Publications, pp. 9295-9302 (Oct. 23, 2012).

* cited by examiner

*Primary Examiner* — Jason McCormack
(74) *Attorney, Agent, or Firm* — Sterne, Kessler, Goldstein & Fox P.L.L.C.

(57) ABSTRACT

Disclosed herein are system, apparatus, article of manufacture, method and/or computer program product embodiments for identifying material. An embodiment includes ionizing, in gas phase, a target substance; creating, in gas phase, a pulse of ionized material from the ionized target substance; injecting the pulse of ionized material into a condensed phase drift medium; and identifying, by at least one processor, the target substance using the pulse of ionized material in the condensed phase drift medium.

21 Claims, 4 Drawing Sheets

HYBRID ION MOBILITY SPECTROMETER

BACKGROUND

Sensing devices are often used to detect the presence of substances ranging from common substances (for example, medical drugs, perfumes, allergens), to illegal substances (for example, narcotics and drugs), to dangerous or threat substances (for example, explosives, chemical warfare agents, bio warfare agents). Due to wide-spread threats and illicit substances and their continuously changing characteristics there is a need for a miniaturized, low cost and high-performance sensing device, especially for detection of trace or residue threat materials. The ease of adaptation or integration with other systems, including platforms and other sensing devices, are also needed for operational effectiveness. Ion Mobility Spectrometry (IMS) is widely used as a robust trace detection device. Existing devices suffer from many problems including performance, size, cost, and ease of use. Low-cost, high-performance and miniaturized IMS will make a major impact in the utility of this sensing modality and significantly enhance its application effectiveness.

SUMMARY

Provided herein are system, apparatus, method and/or computer program product embodiments, and/or combinations and sub-combinations thereof, for identifying materials using ion mobility-based spectrometry.

An embodiment includes a method for identifying material. The method operates by ionizing, in gas phase, a target substance; creating, in gas phase, a pulse of ionized material from the ionized target substance; injecting the pulse of ionized material into a condensed phase drift medium; and identifying, by at least one processor, the target substance using the pulse of ionized material in the condensed phase drift medium.

Another embodiment includes a hybrid ion mobility spectrometer for identifying material. The hybrid ion mobility spectrometer includes a gas phase ionizer, a gas phase gate; a condensed phase drift medium, and a collector. The gas phase ionizer is configured to ionize a targeted substance. The gas phase gate is configured to control the amount of charge and inject a pulse of ionized material from the ionized target substance for a pre-determined gate opening time. The condensed phase drift medium is configured to allow the pulse of ionized material to flow through it. The collector is configured to receive the pulse of ionized material from the condensed phase drift medium and calculate a flight time of the ion pulse through the condensed phase drift medium.

A further embodiment includes a tangible computer-readable device having instructions stored thereon that, when executed by at least one computing device, causes the computing device to perform operations. The operations include ionizing a target substance in gas phase; creating, in gas phase, a pulse of ionized material from the ionized target substance; injecting the pulse of ionized material into a condensed phase drift medium; calculating a velocity of the pulse of ionized material; and identifying, by at least one processor, the target substance by using the velocity.

A further embodiment includes an ion mobility-based spectrometer including a gas phase ionizer configured to ionize a target substance. The ion mobility-based spectrometer further includes a condensed phase cell containing a condensed phase gate and a condensed phase drift cell having a condensed phase drift medium. The condensed phase cell is configured to receive ions from the gas phase ionizer, and the condensed phase drift medium is configured to allow the pulse of ionized material controlled by the gate to flow through the condensed phase drift medium. A collector is configured to receive the ions from the condensed phase drift medium and calculate a flight time.

BRIEF DESCRIPTION OF THE DRAWINGS

The accompanying drawings are incorporated herein and form a part of the specification.

In the drawings, like reference numbers generally indicate identical or similar elements. Additionally, generally, the left-most digit(s) of a reference number can identify the drawing in which the reference number first appears.

DETAILED DESCRIPTION

There is a wide-spread presence of threats and illicit substances that are being transported around the world. These substances can be identified by their different characteristics. What is needed, therefore, is a miniaturized, low-cost, high-performance sensing device that can detect these substances, especially detecting trace or residue material left behind while transporting these substances. In addition, what is needed is an easy way to adapt or integrate these sensing devices into existing other systems, such as platforms or other sensing devices.

Ion Mobility Spectrometry (IMS) is widely used as a robust trace detection device in many scenarios. A low-cost, high-performance and miniaturized IMS will make a major impact in the utility of this sensing modality and significantly enhance its application effectiveness.

Figure 1:
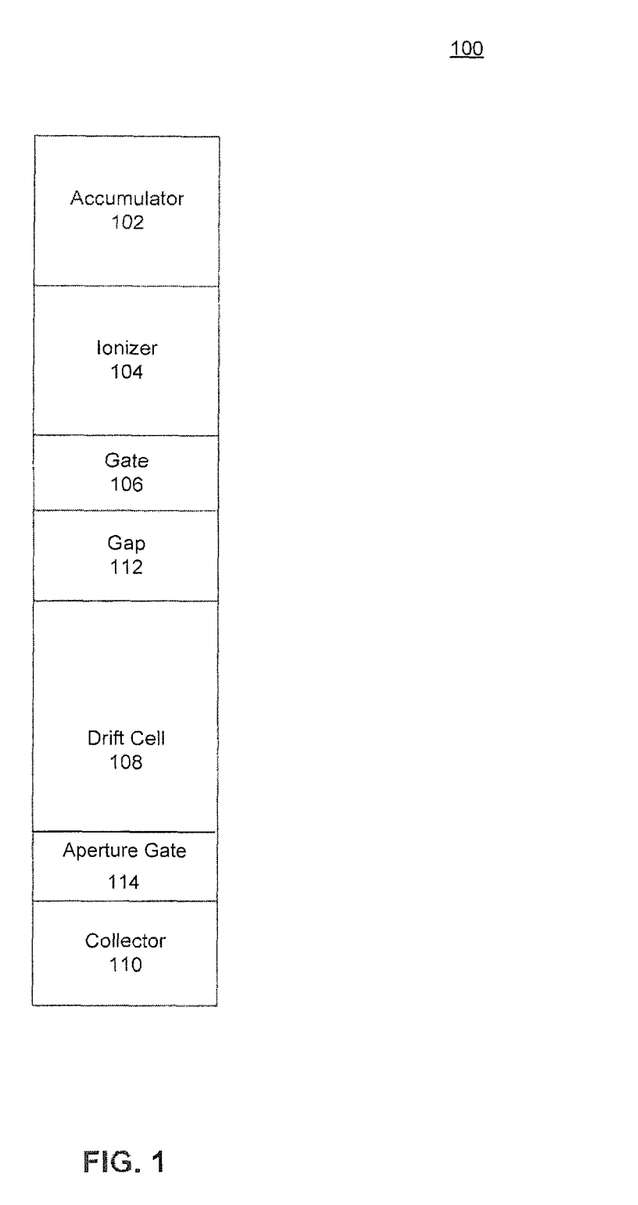
FIG. 1 is a block diagram of an ion mobility spectrometer device that includes an ionizer, a gate, a gap, and a drift cell, according to an example embodiment.

FIG. 1 shows an ion mobility spectrometer device 100 in which embodiments described herein can be implemented. In an embodiment, ion mobility spectrometer device 100 includes an accumulator 102, an ionizer 104, a gate 106, a gap 112, a drift cell 108, and a collector 110.

In an embodiment, ion mobility spectrometer device 100 can be configured to identify a material by gathering material from outside ion mobility spectrometer device 100, ionizing the material, transmitting it through a drift medium, and calculating a time of flight required to traverse the drift medium.

In an embodiment, accumulator 102 can be configured to gather the material. For example, accumulator 102 may include a fan or suction device or other mechanism or means to sample an ambient environment, for example the residue from the surface of an object, near ion mobility spectrometer device 100 that may include a material of interest. In an embodiment, accumulator 102 can be a pre-concentrator, or it can be sampling (by a fan or suction device) volatile materials in the environment.

In an embodiment, ionizer 104 can be configured to ionize the material collected by accumulator 102. For example, material can be ionized by different ionizing sources transferring charges from reactant ions, e.g., radioactive source, corona ionization source, electrospray, and other methods. In order to avoid neutral (non-ionized) material passing through gas phase gate 106 and contaminating the drift medium, neutral particles are swept out of the ionized material by a counter-streaming gas flow. Additionally, ionizing the material in the gas phase avoids the possibility for ionized material to cluster around contaminants during ion formation thereby rendering the materials' identification more difficult. A person skilled in the art would understand that these are merely examples and the material can be ionized and processed in other known ways.

In an embodiment, gate 106 is configured to create a pulse of ionized material. Gate 106 can be configured to act as a shutter allowing charged particles to enter a drift cell 108, described below. In an embodiment, gate 106 can open to allow electrically charged particles to pass through, and then close to stop electrically charged particles from passing through. In another embodiment, gate 106 can be an electric field that can be dynamically adjusted to allow ionized material to pass through it or stop ionized material from passing through it.

In an embodiment, drift cell 108 can contain a neutral drift medium, for example a gas or condensed-phase material, through which the pulse of ionized material released from gate 106 can travel. The condensed-phase material may be in the form of a liquid, gel, thin film, etc. A field, for example a DC electric field, can be applied across drift cell 108. This field can be configured to accelerate the ionized material as it travels across drift cell 108. For example, a set of electrodes can be configured to create a DC electric field that extends in the axial direction, i.e., from gate 106 to collector 110, across drift cell 108.

In an embodiment, collector 110 collects the ionized material. Once the ionized material reaches collector 110, a signal is registered at collector 110. The ion mobility spectrometer device 100 can use this signal to determine the flight time of the ionized material. In an embodiment, the flight time is the time it takes for the ionized material to travel from gate 106 to collector 110.

The flight time can be used to identify the ionized material. The flight time can be characterized as the length of drift cell 108 divided by the constant velocity of the ionized material. The velocity is equal to mobility (usually denoted by the symbol K) multiplied by the electric field. The mobility K of the ionized material is specific to each type of material and is related to the size, shape, and mass of that material. The velocity is therefore specific to each type of material and, if conditions were ideal, any material could be identified by measuring the ionized material's flight time and determining the corresponding mobility K.

In actual systems, though, additional factors or effects may affect flight time. For example, the electric field may not be constant. In an embodiment the local DC electric fields that govern the trajectory of the ionized material can be affected by the ionized material itself. For example, the cloud of ionized material can affect the local DC electric field that is set up by the DC voltage applied on the electrodes. In an embodiment, by controlling the amount of charge injected in the drift region, some of these factors can be mitigated based on the design of ion mobility spectrometer device 100.

In addition, diffusion may affect different ionized particles in different ways. As different ionized material particles travel through the drift medium they may be scattered or diffused in different directions, depending on size, shape, mass, velocity, etc. Diffusion may also vary depending on the drift medium. For example the ionized material or the neutral material within and traveling through the drift medium may diffuse more quickly in a gas phase drift medium than in a liquid- or other condensed-phase drift medium. These additional effects may cause different ionized particles of the same material to reach collector 110 at different times. This is known as the "spread" in the time of flight.

Once the signals are collected from collector 110, an estimated time of flight can be calculated. In an embodiment, the estimated time of flight can correspond to the peak of the distribution of ions, i.e., the flight time for the maximum number of ions of one particular material to reach collector 110.

The level of accuracy of the estimated flight time may determine the ability of ion mobility spectrometer device 100 to differentiate and identify ionized material. Resolving power may be used to indicate this level. In an embodiment, the diffusion-limited resolving power is known to scale in proportion to the square root of the product of the electric field across a drift cell 108 and its length. The ratio of the electric field, E, to number density, N, of the drift medium should be less than about 2 Townsend for approximately constant ion mobility, i.e., mobility independent of the ratio of E/N. Increasing the length of drift cell 108 may increase the resolving power if all other parameters governing broadening of the flight time are held constant.

Likewise, the density of the background drift medium can also increase the resolving power due to the fact that it enables operating the device at much higher voltage than a device with a less dense medium. It is important that the dense medium supports maintaining high voltage across the drift cell and does not result in an electrical breakdown. Converting from a gas phase ion mobility spectrometer device 100 to a liquid phase (or other condensed phase) ion mobility spectrometer device 100 may generally increase resolving power by more than an order of magnitude if the aforementioned scaling holds true and no other effects overwhelm the scaling. As used herein, references to a liquid-phase material are understood to also encompass other condensed-phase materials including gels or thin films.

In addition to analyzing effects along drift cell 108 for ion mobility spectrometer device 100, other factors or effects can be monitored and controlled that also affect resolving power. For example, the time the gate is open to allow a pulse of ionized material to enter drift cell 108 can be a limiting factor. In an embodiment the gate may be opened and closed by modifying an electric field at the gate to either allow ionized particles to pass through it or to stop ionized particles from passing through it. For gas phase ion mobility spectrometer device 100, short pulses can be created by changing the orientation of a field in gate 106 quickly. This is because it only requires a relatively small amount of force to change the direction of travel of ionized material in a gas phase. For liquid phase ion mobility spectrometer device 100 short pulses with sharp rise and fall time (effectively a rectangular pulse) may be difficult to realize. Similar to gas phase ion mobility spectrometry, the orientation of a field in gate 106 can be changed. But, it requires a much higher force (i.e., transverse electric field) to change the direction of flow of ionized material in a liquid or other condensed phase. Thus, realizing a short-pulse gate and controlling the amount of charge flow (from ionization cell to the drift cell) in a liquid or other condensed phase can be much restricted.

Other effects, such as space-charge (Coulomb) effects and image effects near the collector, can also be important. Coulomb effects can be more pronounced in a liquid or other condensed phase. Due to its $1/r^2$ dependency (r being the distance of separation between two charges) Coulomb effects are related to how spread out the ionized material particles are. For liquid phase ion mobility spectrometry, the ionized material particles do not spread out (due to diffusion) as much as gas phase ion mobility spectrometry, and this can manifest as much more pronounced Coulomb effects in liquid or other condensed phases.

In addition, attention may need to be paid to effects near collector 110, such as electrical image effects which may interfere or distort collector 110's response when ionized material approaches collector 110. In an embodiment collector 110 is guarded from the effects of background electrical noise in the system. For example an aperture gate 114 can isolate or protect collector 110 from these deleterious effects. In addition, collector 110 can be configured such that ions, which create an image charge on collector 110, do not affect the ion motion of the oncoming ionized material.

In an embodiment, the repetition rate at which pulses can be created is dependent on the width of this pulse and the length of drift cell 108. This is to avoid faster ions in a later pulse catching up or surpassing slower ions of an earlier pulse. If this were to happen, it would be difficult or even impossible to tell, at collector 110, which responses should be associated with which pulses.

In addition to being important for these effects, resolving power also increases as the width of the gate pulse (i.e., the time the gate allows ions to pass through it) decreases. By reducing the inaccuracy of when an ionized particle's flight time started, a more accurate flight time can be estimated.

An ion mobility spectrometer can be used to detect many materials including both chemical and biological materials, for example explosives, chemical warfare agents, narcotics and drugs, allergens, toxic industrial chemicals, leaked gas, etc. In order to make this technology more viable it can be advantageous to make the spectrometer small, affordable, effective, and efficient.

Figure 2:
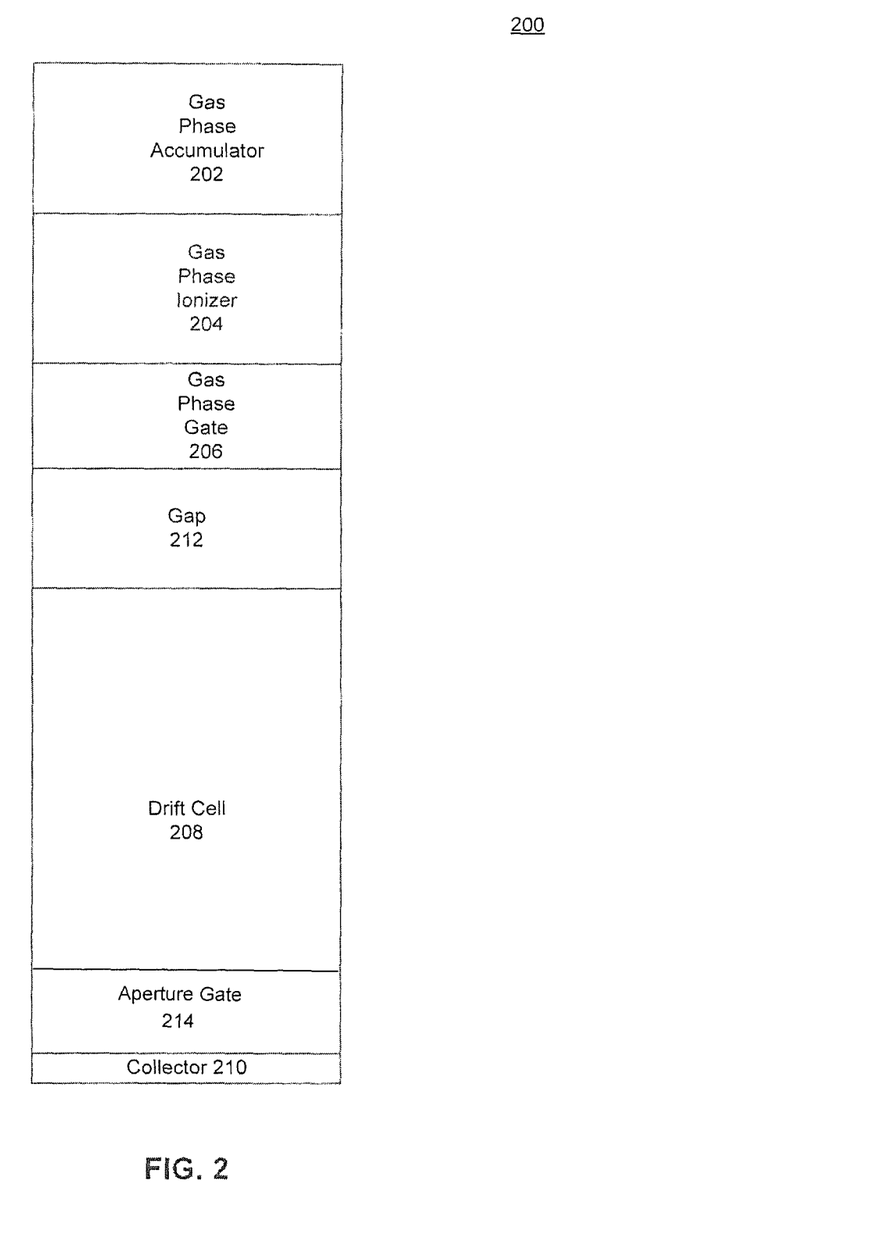
FIG. 2 is a block diagram of a hybrid ion mobility spectrometer device that includes a gas-phase ionizer, a gas-phase gate, a gap and a condensed-phase drift cell according to an example embodiment.

FIG. 2 shows a hybrid ion mobility spectrometer device 200 in which embodiments described herein can be implemented. In an embodiment, hybrid ion mobility spectrometer device 200 includes a gas-phase accumulator 202, gas-phase ionizer 204, a gas phase gate 206, a gap 212, a liquid phase drift cell 208, and a collector 210. In the interest of brevity, the discussion herein generally refers to the drift medium as a liquid but a reader should understand that such references to a liquid-phase material also encompass other condensed-phase materials including gels or thin films.

In an embodiment, hybrid ion mobility spectrometer device 200 can be configured to identify a material by gathering material from outside hybrid ion mobility spectrometer device 200, ionizing and gating the material in gas phase, and transmitting the material through a liquid- or other condensed-phase drift medium, and calculating a time of flight required to traverse the drift medium.

In an embodiment, hybrid ion mobility spectrometer device 200 can be created that has a high resolving power while using a miniaturized device. Hybrid ion mobility spectrometer device 200 takes advantage of the ability to gate ionized material quickly and control charge injection while in gas phase and the ability to improve resolving power while allowing for smaller devices by using liquid phase drift cell 208 that uses a liquid- or other condensed-phase drift medium.

In an embodiment, gas phase accumulator 202, similar to accumulator 102 of FIG. 1, can be configured to gather the material. For example, accumulator 102 may include a fan, suction, or sampling device or other means to gather ambient material near hybrid ion mobility spectrometer device 200 that may include material of interest.

In an embodiment, gas phase ionizer 204 can be configured to ionize the material collected by accumulator 202 while the material is in the gas phase. For example, material can be ionized or charged by different types of ionization sources such as a radioactive source, corona ionization source, electrospray ionization source, etc. A person skilled in the art would understand that these are merely examples, and the material can be ionized in the as phase in other known ways.

In an embodiment, gas phase gate 206 is configured to create a pulse of ionized material and is disposed between an ionized gas and a liquid- or other condensed-phase drift medium located in a liquid phase drift cell 208 (described in more detail below). Gas phase gate 206 can be a Bradbury-Nielsen (B-N) gate, a potential trap gate, or any other suitable gating mechanism. In a preferred embodiment gas phase gate 206 provides a pulse of ionized material, the pulse having a fast rise and fall time and a very narrow pulse width, preferably on the order of milliseconds or less; effective charge control and charge injection when gas phase gate 206 is open; and no charge injection into the drift cell when gas phase gate 206 is closed.

In an embodiment an electric field is applied across gas phase gate 206 to control the flow of ionized material through gas phase gate 206 and into liquid phase drift cell 208. For example, when the electric field in gas phase gate 206 is oriented perpendicularly (i.e. radially) to the longitudinal direction of liquid phase drift cell 208, the ionized material does not cross through gas phase gate 206 and does not enter liquid phase drift cell 208. When the electric field in gas phase gate 206 is oriented in a direction parallel to the longitudinal length of liquid phase drift cell 208, the ionized material follows the electric field through gas phase gate 206 and into liquid phase drift cell 208.

In a preferred embodiment gas phase gate 206 is physically separated from the liquid phase drift medium such that gas phase gate 206 does not contact the liquid phase drift medium, especially if a B-N gate with wires is used. Gas phase gate 206 can therefore quickly and accurately control the space charge injected into liquid phase drift cell 208, and pulse duration and its repetition rate. As illustrated in FIG. 2 by way of example but not limitation, gas phase gate 206 can be physically located above liquid phase drift cell 208, thereby creating a physical gap 212 separating gas phase gate 206 from the liquid phase drift medium in liquid phase drift cell 208. Gap 212 can range in length from a few millimeters for a B-N gate, for example, to close to almost no gap distance for an electrostatic potential trap gate. Other gating devices could have correspondingly small gap lengths.

In an embodiment, liquid phase drift cell 208 receives a pulse of ionized material from gas phase gate 206 and injects or otherwise passes the ionized material into the liquid- or condensed-phase drift medium. In an embodiment desirable characteristics of the liquid- or condensed-phase drift medium include being electrically neutral with a high dielectric constant supporting high voltage; chemically inert or non-reactive; and non-volatile. The length of the liquid drift cell should preferably be held constant.

In an embodiment a uniform electric field is applied axially along the longitudinal length of the drift cell and across the liquid phase drift material such that the ionized material uniformly follows the axial electric field lines through the liquid phase drift material toward collector 210. Collector 210, similar to collector 110 illustrated in FIG. 1, collects the ionized material and generates a corresponding signal in the form of an electrical pulse. As described in more detail herein, the device can use this signal to determine the ionized material's flight time by measuring the time interval that begins when gas phase gate 204 opens and transfers ionized material from ionization cell 204 into liquid phase drift cell 208 and ends when the ionized material stops generating a corresponding signal at collector 210. The flight time of the liquid phase ionized material thus corresponds to the time it takes the ionized material to travel from gas phase gate 206 to collector 210. As previously discussed, precisely determining the flight time is important for accurately identifying ionized material passing through ion mobility spectrometer device 200.

Because the drift medium is in liquid phase the volume of the liquid phase drift medium, and consequently the length of liquid phase drift cell 208, can be relatively small compared to known gaseous-phase ion mobility devices. Liquid phase drift cell 208's small size coupled with other properties of the present invention permits a relatively high voltage to be maintained across liquid phase drift cell 208 during operation. The short length of liquid phase drift cell 208, short pulse width from gas phase gate 206 with effective charge control, uniform electric field through the drift medium, high voltage, and the diffusion properties of the drift medium result in minimal spread of the ionized material as it travels through the drift medium toward collector 210.

An aperture gate 214 in close proximity with the collector reduces any effect due to image charges on the collector on the oncoming ionized materials and also shields the collector from any background electrical noise. In a preferred embodiment aperture gate 214 can be an integral part of the collector. In a preferred embodiment very little or no imperfection or distortion on the pulse of ionized material is introduced during the ionized material's transit through the drift cell. The signal shape from collector 210 then closely corresponds to the shape of the pulse of ionized material entering liquid phase drift cell 208 from gas phase gate 206. The ionized materials' flight time can therefore be accurately determined, leading to increased accuracy in determining the ionized material's identity.

In an embodiment, and as previously described, gas phase gate 206 of hybrid ion mobility spectrometer device 200 can create a pulse with a very short duration, (i.e., the length of time for one pulse of ionized material to pass through gas phase gate 206) and is coupled with a liquid- or other condensed-phase drift medium across which a uniform electric field is applied. The ionized material entering liquid phase drift cell 208 and passing through the relatively short liquid-phase drift medium experiences reduced spread in time (with respect to the drift time corresponding to the peak of the ion pulse) as compared to known gas-phase ion mobility spectrometer devices. Ion mobility spectrometer device 200 thereby achieves significantly improved results with a much smaller size and more operationally efficient and effective device using less power than currently-available ion mobility spectrometer devices. In an embodiment hybrid ion mobility spectrometer device 200 can achieve a resolving power more than approximately one order of magnitude higher than a similarly-sized miniaturized gas phase ion mobility spectrometer device.

By way of example but not limitation an embodiment of hybrid ion mobility spectrometer device 200 may have gas phase gate 206 with dimensions measuring about a square centimeter in area. Liquid phase drift cell 208 may be about a centimeter long and about a centimeter in diameter and consume power of about milliwatt scale. In another embodiment, hybrid ion mobility spectrometer device 200 may be fabricated on a chip-scale, i.e., millimeter-scale dimensions, and require significantly reduced power.

Additionally, in an embodiment hybrid ion mobility spectrometer device 200, due to its generalized attributes, can be constructed in a modular fashion such that gas phase ionizer 204, gas phase gate 206, and liquid phase drift cell 208 can be easily accessed and individually replaced with different elements. In this manner the spectrometer device may be configured to operate in any one of four modes. First, in an all-gas-phase mode when liquid phase drift cell 208 is replaced with a drift cell containing a gas-phase drift medium. In such a configuration gas phase ionizer 204, gas phase gate 206, and the drift cell are each operating in a gaseous phase. Second, in an all-liquid-phase mode when gas phase ionizer 204 and gas phase gate 206 are replaced with a liquid-phase ionizer and a liquid-phase gate. In such a configuration the ionizer, gate, and liquid phase drift cell 208 are each operating in a liquid or other condensed phase. Third, in a hybrid mode in which the ionizer and gate are in gas phase and the drift cell contains a liquid- or other condensed-phase drift medium, as described more fully herein. Fourth, in a further hybrid mode in which gas phase ionizer 204 injects ions into a liquid- or other condensed-phase cell containing a liquid-phase gate. The ions then travel through the liquid-phase gate and into a liquid- or other condensed-phase drift cell. In this arrangement the ions are created in gas phase, and the gate and drift cell are in liquid or other condensed phase.

As explained above, the spectrometer device can be quickly and easily configured to operate in either an all-gas-phase mode, an all-liquid-phase mode, or a hybrid mode having both gas- and liquid-phase components simply by accessing and replacing the spectrometer device's individual elements.

Figure 3:
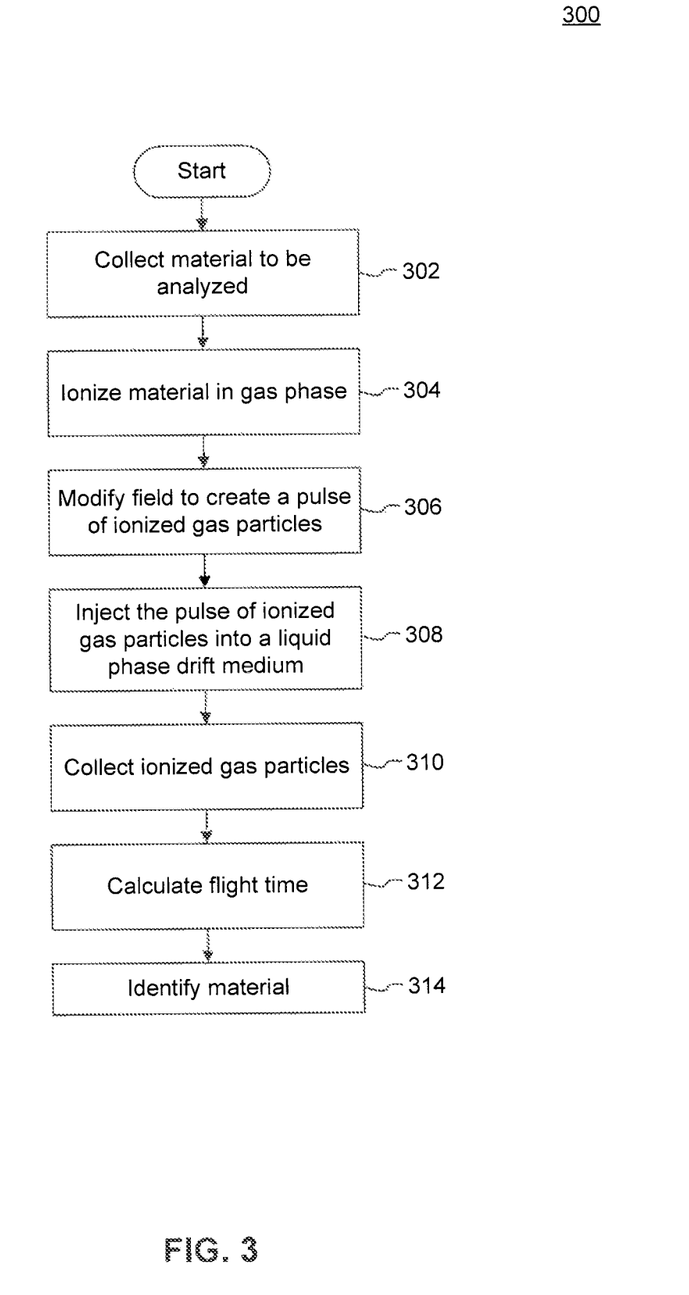
FIG. 3 is a flowchart illustrating a process for identifying a material using a hybrid ion mobility spectrometer device, according to an example embodiment.

FIG. 3 is a flowchart illustrating a process for identifying an unknown material, according to an example embodiment. FIG. 3 shows an example method 300 for identifying an unknown material using a hybrid ion mobility spectrometer device, for example hybrid ion mobility spectrometer device 200 illustrated in FIG. 2. Method 300 can be performed by processing logic that can comprise hardware (e.g., circuitry, dedicated logic, programmable logic, microcode, etc.), software (e.g., instructions run on a processing device), or a combination thereof.

At step 302, in an embodiment, material to be analyzed is collected. For example, this can be collected by gas phase accumulator 202 illustrated in FIG. 2.

At step 304, in an embodiment, the collected material is ionized. For example, the collected material may be subjected to an electric field. In an embodiment, this can be ionized by gas phase ionizer 204 in FIG. 2.

At step 306, in an embodiment, a pulse of ionized material is created. For example, first, an electric field can be created that runs perpendicular to the preferred flow of ionized material. This creates a block through which the ionized material will not flow. Next, the electric field can be modified to run parallel to the preferred flow of ionized material, through the gate. This creates a force that accelerates the ionized material in the direction of the gate towards the collector. Last, the electric field can be modified to again run perpendicular to the preferred flow of ionized material. This creates a block through which the ionized material will not flow, creating the end of the pulse. For example, this pulse can be created by gas phase gate 206 illustrated in FIG. 2.

At step 308, in an embodiment, the pulse of ionized material is injected into the liquid- or other condensed-phase drift cell. The liquid phase drift cell includes a liquid- or other condensed-phase drift medium that is electrically neutral. This allows the ionized material within the pulse to travel towards the gate accelerated by the field. For example, the ionized material can be accelerated by a DC electric field that runs towards the collector. For example, the ions released by gas phase gate 206 can be injected into liquid phase drift cell 208 illustrated in FIG. 2.

At step 310, in an embodiment, once the ionized material reaches the collector, the ionized material is collected. This can include collecting signals that are released from the collector when ionized material particles each reach the collector. For example, this can be collected by collector 210 illustrated in FIG. 2.

At step 312, in an embodiment, an estimated flight time is calculated. Based on when the pulse of ionized particles is injected into the drift cell and when those ionized particles reached the collector, a flight time can be estimated. By narrowing the width of the pulse (i.e., gate opening time), the accuracy of the estimate can be increased. The determination of when an ionized material particle would have reached the collector can be calculated in multiple ways. For example, an average of all collection times can be used. In another example, certain outliers can be removed. In another example, estimates, for example statistical estimates, can be used to more accurately process the data. In another example, the estimated time of flight can correspond to the peak of the distribution of ions, i.e., the flight time for the maximum number of ions of one particular material that reach the collector At step 314, in an embodiment, the ionized material is identified based on the flight time. The velocity can be calculated from the length of the device and the flight time. The velocity can be used to calculate the mobility of the ionized material. The calculation of the mobility can be extremely accurate due to the high resolving power achieved by a hybrid ion mobility spectrometer and its ability to differentiate materials with close mobility values. That mobility can provide information regarding the size, shape, and mass of the ion. Thus, the hybrid ion mobility spectrometer can be used to more accurately identify materials.

It is understood that the present invention has been described herein with reference to ion mobility spectrometry but the invention is also applicable to, and usable with, differential mobility spectrometry or any other separation method based upon ion mobility.

Example Computer System

Figure 4:
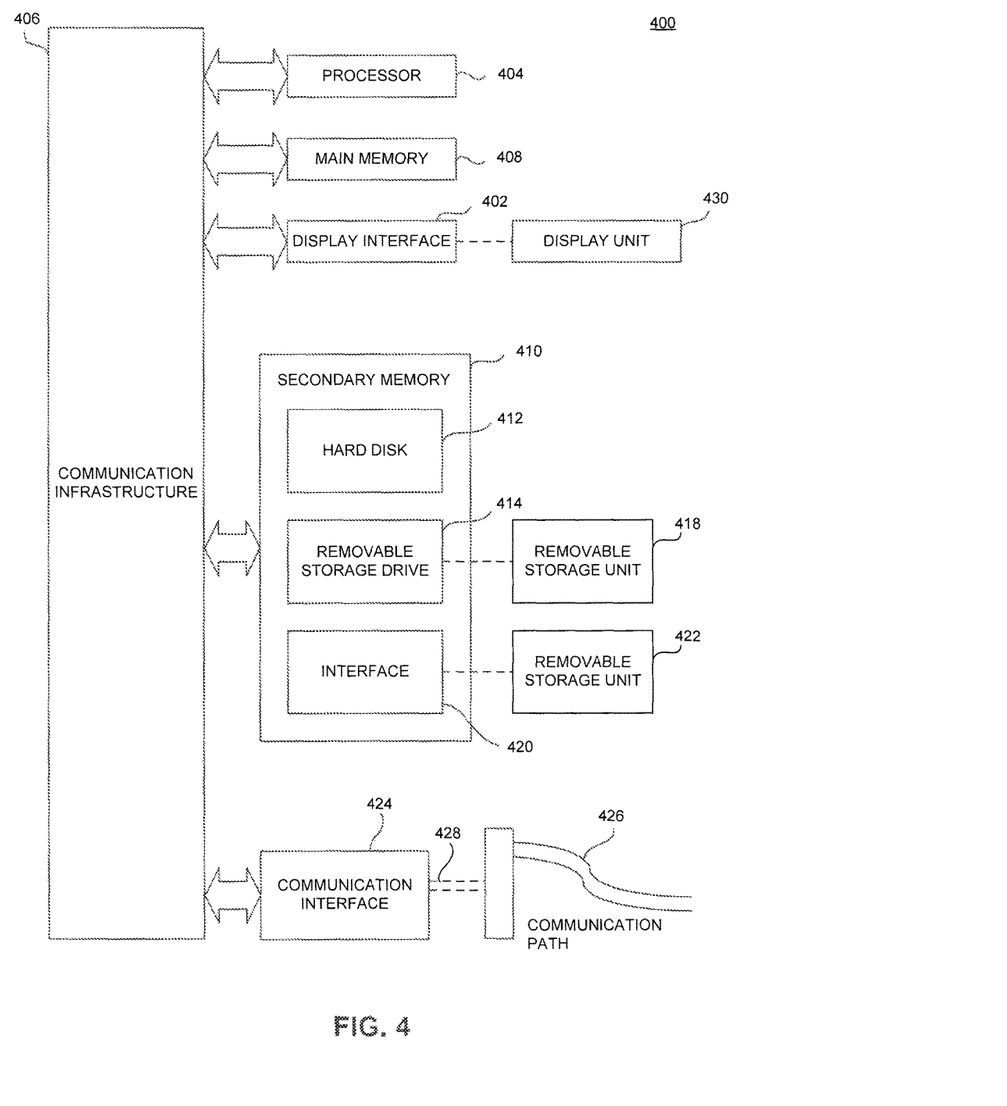
FIG. 4 is an example computer system useful for implementing various embodiments.

Various embodiments can be implemented, for example, using one or more well-known computer systems, such as computer system 400 shown in FIG. 4. Computer system 400 can be any well-known computer capable of performing the functions described herein, such as computers available from International Business Machines, Apple, Sun, HP, Dell, Sony, Toshiba, etc.

Computer system 400 includes one or more processors (also called central processing units, or CPUs), such as a processor 404. Processor 404 is connected to a communication infrastructure or bus 406.

One or more processors 404 may each be a graphics processing unit (GPU). In an embodiment, a GPU is a processor that is a specialized electronic circuit designed to rapidly process mathematically intensive applications on electronic devices. The GPU may have a highly parallel structure that is efficient for parallel processing of large blocks of data, such as mathematically intensive data common to computer graphics applications, images and videos.

Computer system 400 also includes user input/output device(s) 403, such as monitors, keyboards, pointing devices, etc., which communicate with communication infrastructure 406 through user input/output interface(s) 402.

Computer system 400 also includes a main or primary memory 408, such as random access memory (RAM). Main memory 408 may include one or more levels of cache. Main memory 408 has stored therein control logic (i.e., computer software) and/or data.

Computer system 400 may also include one or more secondary storage devices or memory 410. Secondary memory 410 may include, for example, a hard disk drive 412 and/or a removable storage device or drive 414. Removable storage drive 414 may be a floppy disk drive, a magnetic tape drive, a compact disk drive, an optical storage device, tape backup device, and/or any other storage device/drive.

Removable storage drive 414 may interact with a removable storage unit 418. Removable storage unit 418 includes a computer usable or readable storage device having stored thereon computer software (control logic) and/or data. Removable storage unit 418 may be a floppy disk, magnetic tape, compact disk, DVD, optical storage disk, and/ any other computer data storage device. Removable storage drive 414 reads from and/or writes to removable storage unit 418 in a well-known manner.

According to an exemplary embodiment, secondary memory 410 may include other means, instrumentalities, or other approaches for allowing computer programs and/or other instructions and/or data to be accessed by computer system 400. Such means, instrumentalities, or other approaches may include, for example, a removable storage unit 422 and an interface 420. Examples of the removable storage unit 422 and the interface 420 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 400 may further include a communication or network interface 424. Communication interface 424 enables computer system 400 to communicate and interact with any combination of remote devices, remote networks, remote entities, etc. (individually and collectively referenced by reference number 428). For example, communication interface 424 may allow computer system 400 to communicate with remote devices 428 over communications path 426, which may be wired and/or wireless, and which may include any combination of LANs, WANs, the Internet, etc. Control logic and/or data may be transmitted to and from computer system 400 via communication path 426.

In an embodiment, a tangible apparatus or article of manufacture comprising a tangible computer useable or readable medium having control logic (software) stored thereon is also referred to herein as a computer program product or program storage device. This includes, but is not limited to, computer system 400, main memory 408, secondary memory 410, and removable storage units 418 and 422, as well as tangible articles of manufacture embodying any combination of the foregoing. Such control logic, when executed by one or more data processing devices (such as computer system 400), causes such data processing devices to operate as described herein.

Based on the teachings contained in this disclosure, it will be apparent to persons skilled in the relevant art(s) how to make and use the invention using data processing devices, computer systems and/or computer architectures other than that shown in FIG. 4. In particular, embodiments may operate with software, hardware, and/or operating system implementations other than those described herein.

CONCLUSION

It is to be appreciated that the Detailed Description section, and not the Summary and Abstract sections (if any), is intended to be used to interpret the claims. The Summary and Abstract sections (if any) may set forth one or more but not all exemplary embodiments of the invention as contemplated by the inventor(s), and thus, are not intended to limit the invention or the appended claims in any way.

While the invention has been described herein with reference to exemplary embodiments for exemplary fields and applications, it should be understood that the invention is not limited thereto. Other embodiments and modifications thereto are possible, and are within the scope and spirit of the invention. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments may perform functional blocks, steps, operations, methods, etc. using orderings different than those described herein.

References herein to "one embodiment," "an embodiment," "an example embodiment," or similar phrases, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein.

The breadth and scope of the invention should not be limited by any of the above-described exemplary embodiments, but should be defined only in accordance with the following claims and their equivalents.

What is claimed is:

1. A method for identifying material, comprising:
   ionizing, in gas phase, a target substance;
   creating, in gas phase by a gate, a pulse of ionized material from the ionized target substance;
   injecting the pulse of ionized material, through a gap, into a condensed phase drift medium, wherein a length of the gap is based on a type of the gate; and
   identifying, by at least one processor, the target substance using the pulse of ionized material in the condensed phase drift medium.

2. The method of claim 1, wherein the gap separates the gate from the condensed phase drift medium.

3. The method of claim 2, wherein the gate uses electric fields to create the pulse of ionized material.

4. The method of claim 1, further comprising:
   determining a flight time of the pulse of ionized material based on when the pulse of ionized material is injected in the condensed phase drift medium and when the pulse of ionized material reaches a collector, wherein the collector is located at one end of the condensed phase drift medium, opposite of where the pulse of ionized material is injected into the condensed phase drift medium.

5. The method of claim 4, wherein the identification uses the flight time of the pulse of ionized material.

6. The method of claim 4, further comprising guarding, by an aperture gate, the collector from electrical noise and image charge.

7. The method of claim 1, wherein a direct current electric field is created and applied in an axial direction from the gate through the gap and across the condensed phase drift medium to a collector.

8. The method of claim 1, further comprising collecting the ionized target substance.

9. The method of claim 1, wherein the condensed phase drift medium comprises an electrically neutral material.

10. A hybrid ion mobility spectrometer, comprising:
    a gas phase ionizer configured to ionize a targeted substance;
    a gas phase gate configured to control the amount of charge and inject a pulse of ionized material from the ionized target substance;
    a condensed phase drift medium configured to allow the pulse of ionized material to flow through it;
    a gap configured to separate the gas phase gate from the condensed phase drift medium, wherein a length of the gap is based on a type of the gas phase gate; and
    a collector configured to receive the pulse of ionized material from the condensed phase drift medium and calculate a flight time.

11. The hybrid ion mobility spectrometer of claim 10, wherein the gas phase ionizer produces ions of target substance by transferring charges from reactant ions.

12. The hybrid ion mobility spectrometer of claim 10, wherein the gas phase gate uses electric fields to create the pulse of ionized material.

13. The hybrid ion mobility spectrometer of claim 10, wherein the condensed phase drift medium comprises a charge-neutral material.

14. The hybrid ion mobility spectrometer of claim 10, wherein the collector is configured to use the calculated flight time to identify the targeted substance.

15. The hybrid ion mobility spectrometer of claim 10, further comprising an aperture gate configured to guard the collector from electrical noise and also shields the ion pulse from an image charge on the collector.

16. The hybrid ion mobility spectrometer of claim 10, further comprising a field generator configured to create an electric field across the condensed phase drift medium.

17. The hybrid ion mobility spectrometer of claim 10, wherein the condensed phase drift medium is further configured to allow the pulse of ionized material to travel at a constant velocity and be collected at the collector.

18. An ion mobility-based spectrometer, comprising:
a gas phase ionizer configured to ionize a target substance;
a condensed phase cell containing a condensed phase gate and a condensed phase drift cell having a condensed phase drift medium, the condensed phase cell being configured to receive ions from the gas phase ionizer, and the condensed phase drift medium being configured to allow the pulse of ionized material controlled by the condensed phase gate to flow through the condensed phase drift medium;
a gap configured to separate the gas phase ionizer and the condensed phase gate from the condensed phase drift medium;
a plurality of electrodes configured to apply an electric field in an axial direction through the gap and along a longitudinal length of the condensed phase drift cell across the condensed phase drift medium;
a collector configured to receive the ions from the condensed phase drift medium and calculate a flight time.

19. The method of claim 1, wherein the type of the gate is an electrostatic potential trap gate and the length of the gap is substantially zero.

20. The method of claim 1, further comprising controlling, by the gate, a property of the pulse of ionized material wherein the controlling is based on the length of the gap and the property includes at least one of a space charge, a pulse duration, and a repetition rate.

21. The ion mobility-based spectrometer of claim 18, wherein a length of the gap is based on a type of the condensed phase gate.

\* \* \* \* \*